United States Patent [19]
Frei et al.

[11] Patent Number: 5,143,079
[45] Date of Patent: Sep. 1, 1992

[54] APPARATUS FOR DETECTION OF TUMORS IN TISSUE

[75] Inventors: Ephraim Frei, Jerusalem; Mordechai Moshitzky, Rehovot, both of Israel

[73] Assignee: Yeda Research and Development Company Limited, Rehovot, Israel

[21] Appl. No.: 561,530

[22] Filed: Aug. 1, 1990

[30] Foreign Application Priority Data

Aug. 2, 1989 [IL] Israel ............................. 91193

[51] Int. Cl.⁵ .................................... A61B 5/05
[52] U.S. Cl. ........................................ 128/734
[58] Field of Search ............... 128/653 R, 639, 642, 128/734

[56] References Cited

U.S. PATENT DOCUMENTS

| | | | |
|---|---|---|---|
| 3,778,657 | 12/1973 | Kubo et al. | 313/367 |
| 4,291,708 | 9/1981 | Frei et al. | 128/734 |
| 4,441,123 | 4/1984 | Ochi | 358/44 |
| 4,458,694 | 7/1984 | Sollish et al. | 128/734 |
| 4,486,835 | 12/1984 | Bai et al. | 128/734 |
| 4,537,203 | 8/1985 | Machida | 128/734 |
| 4,951,674 | 8/1990 | Zanakis et al. | 128/653 R |
| 4,955,383 | 9/1990 | Faupel | 128/734 |

Primary Examiner—Ruth S. Smith
Attorney, Agent, or Firm—Fleit, Jacobson, Cohn, Price, Holman & Stern

[57] ABSTRACT

Improvements in apparatus for detecting tumors in living human breast tissue comprising means for determining the dielectric constants of localized regions of living humans breast tissue including a multiplicity of hexagonal probe elements.

7 Claims, 5 Drawing Sheets

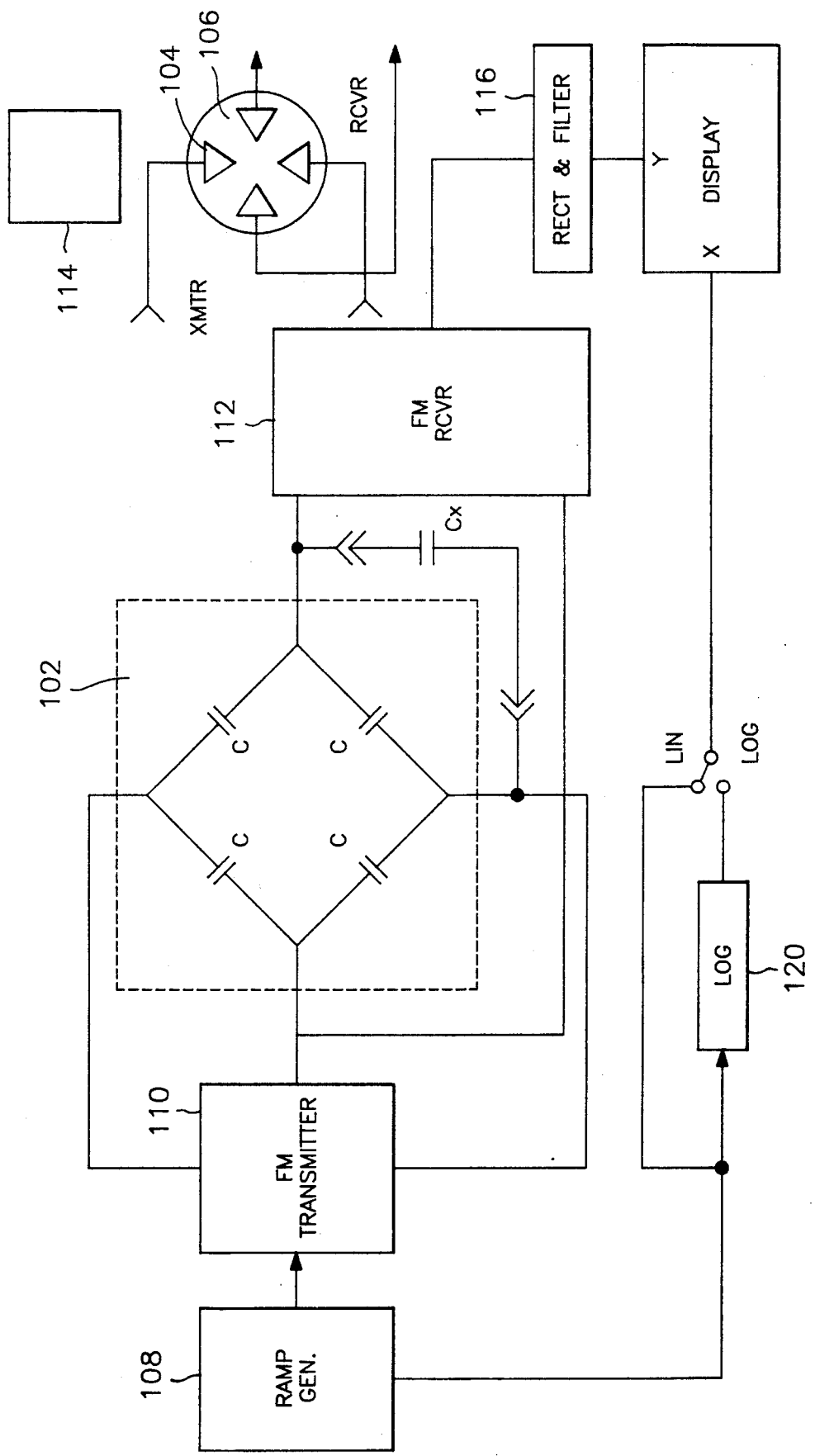

APPARATUS FOR DETECTION OF TUMORS IN TISSUE

FIELD OF THE INVENTION

The present invention relates to improvements in apparatus and methods for the detection of tumors in living human tissue generally, and in particular to the early detection of human breast cancer.

BACKGROUND OF THE INVENTION

Breast cancer is one of the most pernicious diseases in women. This disease, which is the most common cancer of women in the Western world and which now attacks one woman in 13, has had a stationary death rate for many years in spite of advances in surgical techniques, radiotherapy and chemotherapy. Statistics show that about 50% of the women succumb to it, in general from the so called metastases.

Therapy of cancer can have much better success the earlier the cancer is detected. Furthermore surgery can be minor if detection is early, avoiding much suffering. It is known that our present methods of surgery, radiotherapy and chemotherapy are effective for long-term survival if applied when the disease is localized to the breast. Since many of the breast cancer cases are not localized when first seen by the clinician, a way must be found to have women present themselves for examination with their disease at an earlier stage than is commonly the case. This means, in a practical way, detection of preclinical cancer in apparently "well" women, when the disease is unsuspected by patient or physician as is the case in mass screening.

There are usually two steps in the diagnosis of breast cancer. First the detection of a lesion by a screening method or by self-detection, and then narrowing down the diagnosis, first by non-invasive methods and finally by biopsy, which when positive, is mostly followed by immediate surgical intervention. Such factors as time of examination, radiation dose or cost of the study assume minor roles when evaluating a lesion which has already been detected.

In screening for breast cancer, a large number of women, who presumably have no disease or have only minimal symptoms, are involved in the program. These women would not be having the examination, were it not for the opportunity offered by the screening program. The major thrust in screening is not, therefore, differential diagnosis of a lesion, but the step preceding that, i.e. the detection of an abnormality. All one does in mass screening must be directed to the following objective: the initial detection of an abnormality in the simplest, safest, most accurate and most economical manner possible.

At present the following methods are used for the detection of breast cancer in most clinics: (1) Clinical examination including: a. Manual palpation; b. Appearance of the skin; c. Deformation of the breast; (2) X-rays (there are several variants available); (3) Thermography; (4) Transillumination; (5) Ultrasonics.

None of these methods is satisfactory by itself, neither are combinations of these methods fully satisfactory. Cancerous tumors are detected in most cases when several years old. It should also be added that final and reliable diagnosis is only done by biopsy. In many institutions positive diagnosis is obtained in only 25% of biopsies done. It seems therefore obvious that better physical methods for screening of a large number of patients as well as more reliable diagnosis before biopsy would be very important. These methods should also be comfortable and not induce some hesitation in women to visit periodically the clinic. They should also be repeatable any number of times and should not encompass even small health hazards (as X-rays do). The present technology and the large number of patients involved make computer aided devices methods of choice.

Of the presently used methods only thermography lends itself to computerized automation. Success is limited, however, by the rather small number of tumors that cause a rise in temperature of the skin.

U.S. Pat. No. 4,291,708 which is hereby incorporated by reference in its entirety, discloses an apparatus for detecting tumors in living human breast tissue comprising: a device for determining the dielectric constants of a plurality of localized regions of living human breast tissue including a balancing bridge having means for automatically nulling the balancing bridge while in operation; a device for measuring variations in dielectric constants over a plurality of regions and for indicating the possible presence of a tumor as a result of the measurement, a device for applying a swept frequency signal to the probe, and signal processing circuitry, coupled to the balancing bridge for providing an output indication of dielectric constant of the localized region of breast tissue associated with the probe.

U.S. Pat. No. 4,458,694, which is he by reference in its entirety, discloses an apparatus for detecting tumors in living human breast tissue comprising: (a) a device for determining the dielectric constants of localized regions of living human breast tissue including a probing component comprising a multiplicity of probe elements; (b) a device for applying an AC signal to the tissue; and (c) a device for sensing electrical properties at each of said probe elements at a plurality of different times; and (d) signal processing circuitry, coupled to said sensing device for comparing the electrical properties sensed at the plurality of different times for providing an output indication of the dielectric constant of the localized region of breast tissue associated with said probing component.

The probe elements are applied to human breast tissue in vivo, such that individual ones of said probe elements are arranged for sensing characteristics of individual localized regions of human breast tissue.

We have now discovered that when the probe elements have an hexagonal structure, much better results are obtained with the diagnosis made by use of the apparatus described in the above patents.

SUMMARY OF THE INVENTION

The present invention provides a multielement probe for use in apparatus for detecting tumors in living human tissues based essentially on the determination of the dielectric constant and/or the conductivity values of localized regions of said human tissue, said probe comprising a plurality of planar hexagonal electrodes in a closely spaced geometric pattern, each of the electrodes being connected with a suitable circuitry.

The invention also provides apparatus for detecting tumors in living human tissues, in particular apparatus as described in U.S. Pat. Nos. 4,291,708 and 4,458,694 for detecting breast cancer, comprising the multielement planar hexagonal electrodes of the invention.

BRIEF DESCRIPTION OF THE DRAWINGS

FIG. 6 illustrates a schematic block diagram of a detector circuit used with a probe for detecting tumors.

DETAILED DESCRIPTION OF THE INVENTION

Figure 4:
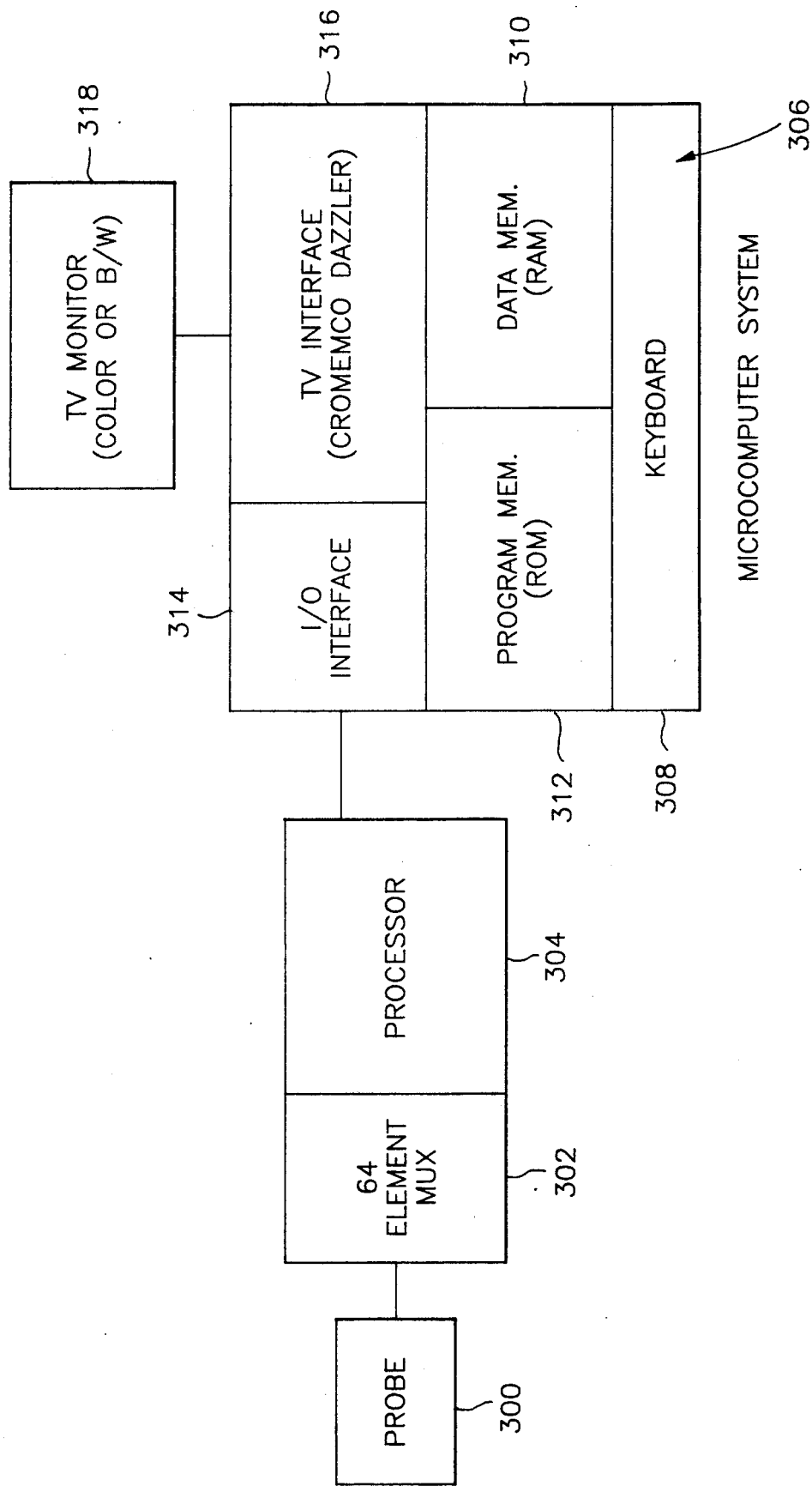
FIG. 4 illustrates a schematic block diagram of a computer-controlled breast cancer screening apparatus of the prior art.

FIG. 4 illustrates in schematic block diagram form a computer-controlled breast cancer screening apparatus as is known in the art form U.S. Pat. No. 4,458,694. The screening apparatus comprises a multielement probe, typically comprising 64 elements arranged in an 8×8 array. Probe 300 is coupled, via a 64 element multiplexer 302 to an electronic processor 304. Electronic processor 304 interfaces with a microcomputer control and data storage and display system 306. System 306, is embodied in a SOL 20 unit, manufactured by Processor Technology of California, U.S.A. It is to be understood of course that any other suitable microcomputer control and data storage and display system may alternatively be employed.

The SOL 20 microcomputer system is based on the Intel 8080 8-bit microcomputer and employs the well-known S-100 bus system. The SOL 20 has a built-in keyboard 308 which permits the entry of patient identification information, for example, and a 16K byte RAM memory 310, such as a Dynabyte DY-M51645, for data storage. A program memory 312 comprises one or more 16K programmable ROM boards such as Cromemco CR-16K PR/A, each having 16K bytes of erasable ROM memory. The SOL-20 also comprises serial and parallel input-output interfaces 314. A video interface 316, the TV Dazzler, (C/CRDZ/A), also manufactured by Cromenco, is provided to generate appropriate video signals for display on a color or black and white television monitor.

The microcomputer system 306 is programmed by standard techniques to generate the required control signals for the electronic processor, to input the data obtained by the electronic processor 304 from the probe 300, and to output the data onto the TV monitor 318 in alphanumeric and graphic grey scale or multicolor format.

The invention provides a multielement probe for use in an apparatus for detecting tumors in living human tissues based essentially on the determination of the dielectric constants and/or conductivity values of localized regions of such tissues, which probe comprises a plurality of plane hexagonal electrodes in a closely spaced geometric pattern, each of the electrodes being connected with suitable circuitry. The hexagonal electrodes are part of a printed circuit pattern.

A tumor detection system comprising said multielement probe is provided which contains a device for applying an AC signal to the tissue beneath each such electrode, a device for sensing the electrical properties of such tissue, and signal processing circuitry providing an output indicative of the dielectric properties of each such region of the tissue. It may also comprise a device for the repetitive application of such AC signals, and for evaluating the resulting signals, determining dielectric properties of regions of the tissue beneath each electrode sensor.

It has been found that fatty tissue exhibits significantly different dielectric constant and conductivity than muscle tissue. Since most cancer develops in post-menopausal women (assumed in the age 50 and up group), and since the post-menopausal breast is characterized by a proliferation of adipose (fatty tissue, it may be possible to detect cancer in the post-menopausal breast by in situ measurement of the appropriate electrical parameters. It is assumed, therefore, that the problem of detecting a tumor in the breast reduces to that of detecting a small region characterized by certain electrical characteristics embedded in a larger region of different electrical characteristics (essentially, those of fat).

The present devices provide means of measurement of dielectric constant and conductivity in the breast. By examining different portions of the breast, and by comparing the dielectric constants and conductivities measured, a region containing a possible tumor can be identified through changes in dielectric constant and/or conductivity.

The electric field E within the breast due to the applied external field supplied by the probe satisfies the Laplace equation: $\nabla^2 E = 0$. At every location within the breast, the dielectric displacement D is related to the electric field E by the complex dielectric constant $\epsilon$ as $D = \epsilon E$. The complex dielectric constant includes a real part (the dielectric constant) and an imaginary part, the losses, related to conductivity.

Different dielectric constants within the breast combine to influence the impedances as measured by the multielectrode probe, according to the Laplace equation and the appropriate boundary conditions. Hereinafter in the specification and the claims, the term dielectric constant shall be taken to mean the complex dielectric constant, the real or imaginary part thereof or electrical properties related thereto.

The purpose of the invention is therefore to enable detection of possible tumors in the breast. The method is safe, non-invasive, and does not require injection of contrast materials. The devices provided give quantitative information which can be used in conjunction with any or all of the present-day diagnostic techniques (palpation, X-ray, thermography). Finally, it can be used as a prescreening technique before a decision is taken to send the screenee to mammography.

The probe comprises hexagonal electrodes arranged in consecutive rows, where the hexagonal elements in any consecutive row are displaced respective to the preceding row by half the width of the hexagon. There are also provided a device for switching from one sensor to a predetermined number of sensors, and a device for evaluating the results of such varying sensors. The measurements are made using 1, 3, 5 or 7 electrodes, or with any combination of such electrode sensors at any given time.

The main information needed is obtained by findings of inhomogeneities in the breast. The impedance of a specific area depends on the dielectric constant and the conductivity of the tissue, as well as on the spatial relations of any entity of tissue to its surrounding tissue and the measuring electrode. No definite values can be associated with specific pathologies, even inside a tumor the values vary according to stages of development. Healthy tissue is in general fairly homogeneous.

Whereas in the use of single electrodes, circular electrodes are preferred, for dielectric measurements of the type dealt with in this application, there have been used electrodes comprising a plurality of square elements arranged in a closely arranged geometrical arrangement with little space between adjoining electrode elements. One example is a square shaped probe made of polyvinylchloride plastic that is placed by the operator on the breast of the patient; the active area of the probe contains an 8×8 matrix of square electrodes (of 7 mm each side); the electrodes are gold plated printed copper.

According to the present invention there are provided electrodes for the same use, which have advantageous electrode elements, each of which is connected to the monitoring device.

There exist various alternatives for such arrangements. One of these is set out in FIG. 1, where rows of hexagonal elements are arranged in a pattern with a rectangular outline. The hexagons of the first row nearly touch each other along parallel sides, the second row is displaced to provide a fitting pattern, the third row is like the first one, the fourth row like the second and so on. In this way, one gets more use of the useful electrode area against the useless interelectrode area. Better definition in area and more indepth resolution will result. The outline is within the confines of a rectangle, but without straight-line boundaries, which define a meandering path.

Figure 1:
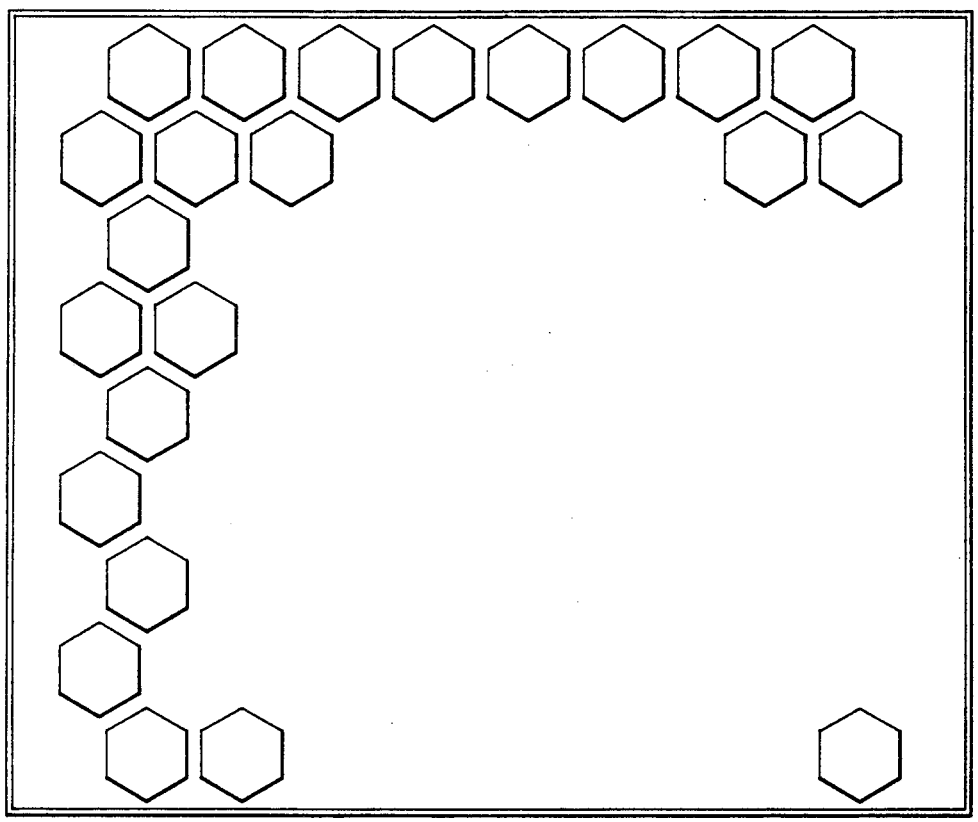
FIG. 1 is a schematic top view of an electrode pattern of the invention.

The pattern of FIG. 1 results in an increased efficiency of the measurement and better utilization of electrode area, with a better indepth resolution. Such advantage results from several factors. The borders of the electrodes or in most cases the unavoidable space between results in a loss of measurement capability. This results from the LaPlace equation which governs the electric fields created with these electrodes. Therefore a shape of maximum area to minimum border is best. On the other hand, the electrodes must have a shape that covers the field, in other words they must fit together. If one wants to use only one geometric type of electrode, hexagonal are superior to square ones. Although a combination of different shapes could be better in this respect, it would create difficulties in the handling of currents to be supplied to such a combination of electrodes, the handling of information derived from these, and therefore would result in very complicated and more costly computing means.

Figure 2:
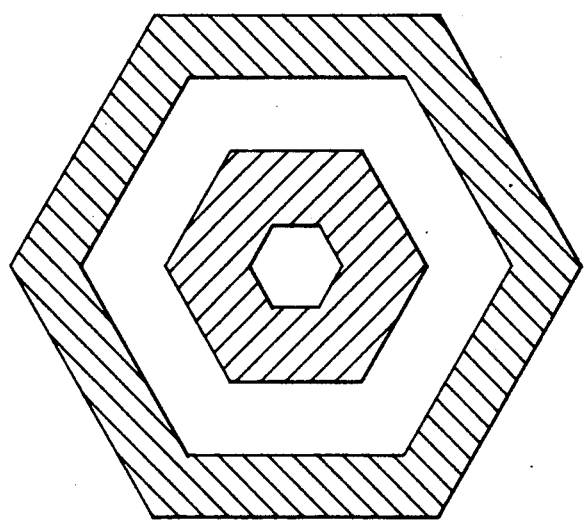
FIG. 2 is a top view of a hexagonal electrode element.
Figure 3A:
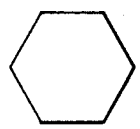
FIGS. 3a to 3d illustrate various electrode patterns comprising hexagonal elements of the invention.
Figure 3B:
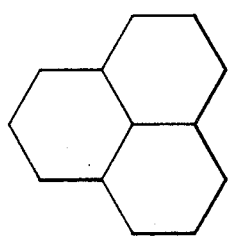
Figure 3C:
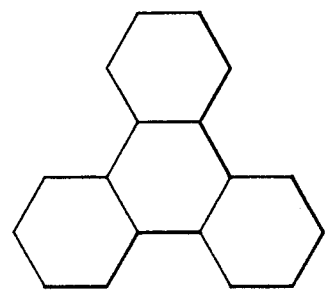
Figure 3D:
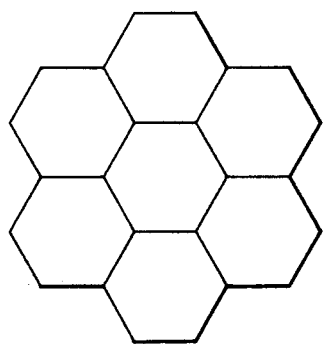
Figure 3E:
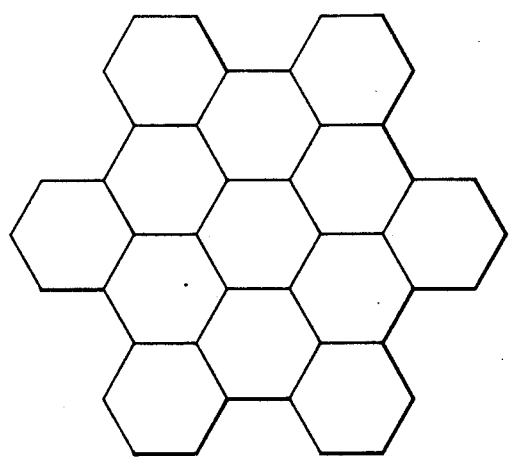

Another consideration to give preference to hexagonal electrodes is the field distortion, which results from the border of the electrodes, the so-called "edge effect" (in German Rand Effekt). This effect propagates into the field increasingly according to the LaPlace equation, and blurring occurs with increasing depth. This means that for investigation near to the surface (skin), one should use a probe with small electrodes, whereas for deeper depths, larger electrodes should be used, as they give better penetration. It would be most inconvenient and a waste of time to change from one probe to the other. It is possible to have the computer circuitry connect several electrodes together in ever increasing numbers. This can give images of ever increasing depths. On the monitoring screen this can also be represented by using differing colors for different depths or alternatively by having each "pixel" consist of different rings analogous to the different depths, as shown in FIG. 2.

Figure 5:
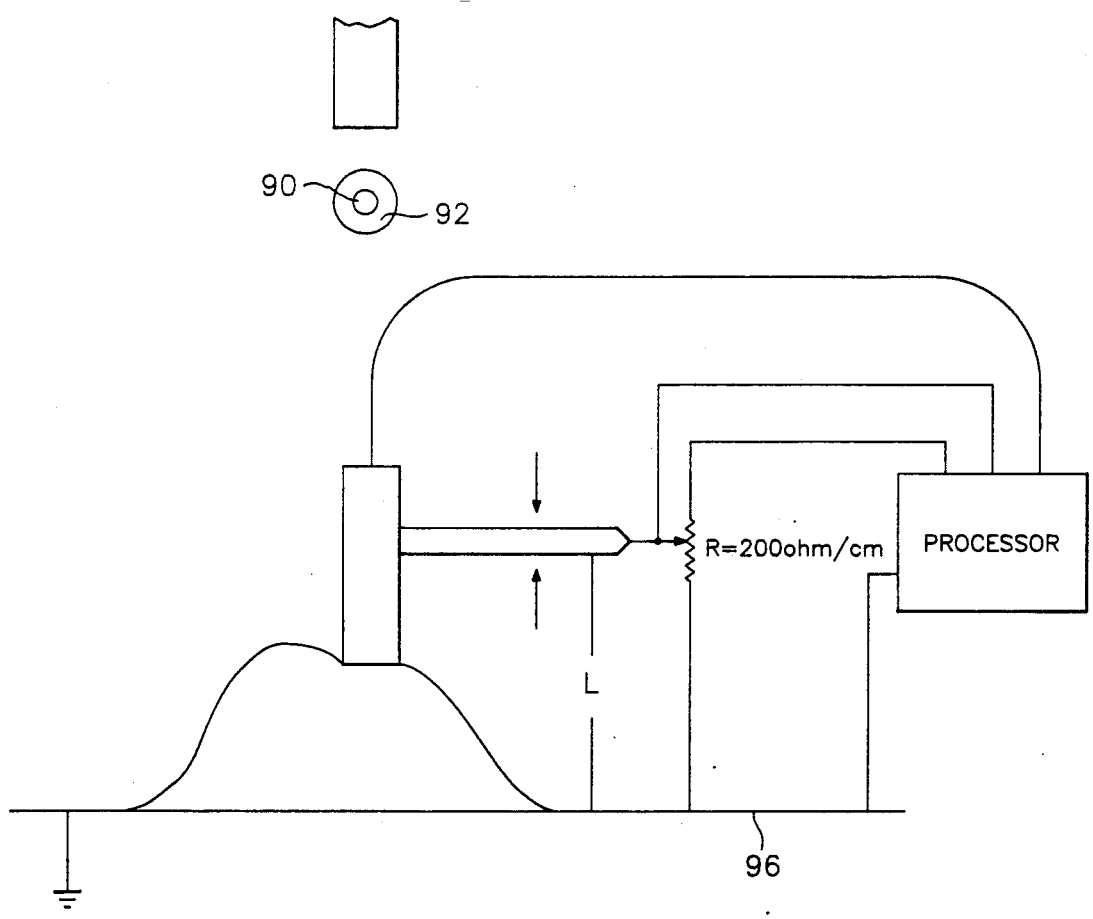
FIG. 5 schematically illustrates a probe of the invention, in use.

FIG. 5 shows, schematically, a probe arrangement which may be useful in the invention. A 1 sq. cm. area circular stainless steel electrode 90 is encased in a layer 92 of PVC or any other suitable insulator. The patient is disposed against a grounded plate or table, as indicated schematically by the grounded plane 96. The probe is placed in contact with the body part and moved from position to position thereon in order to determine the values of the body capacitance and conductance for the various regions of the portion being examined.

At the frequencies used, from about 10 MHz, the capacitance effect is predominant is tissues. FIG. 6 shows a detector based on a capacitance bridge arrangement 102. The capacitance bridge 102 comprises four triangular shaped electrodes 104, arranged in a symmetric fashion on insulating material 106 (typically PVC or Teflon) forming one end of cylindrical probe 114. A ramp generator 108 is used to modulate the carrier frequency of a 100 MHz FM transmitter with a 1 kHz audio modulator whose output is fed to two opposing bridge elements. An FM receiver 112 is connected across the other two opposing bridge elements. A rectifier and filter 116 connected across the audio output of the FM receiver gives a DC voltage proportional to the audio output.

Before the probe is placed on the tissue to be examined, the bridge is balanced and the DC output of rectifier 116 is zero. When the probe is placed over tissue of an inhomogeneous nature (with respect to the dielectric constant), the bridge becomes unbalanced, producing a DC output at rectifier 116. This output is fed to the Y-axis of storage display 118. Simultaneously, the ramp voltage due to 108 is fed to the X-axis of the display to give a display of $C_x$ against $\omega$ or if the logarithmic amplifier 120 is inserted, a display of $C_x$ against log $\omega$ results.

Hexagonal electrodes have the advantage that they allow inter-connection for depth penetration in smaller steps (1,3,6,7), whereas square electrodes allow grouping only in larger steps (1,4,9), as long as one keeps to the condition of maximum area to minimum border (see FIGS. 3a-3d).

The part close to the skin is represented by the center of the pixel, the outer part by depth information, adjacent pixels will then, in many cases, have a similar coloring in the outer rings, conforming to the ever lower definition with depth. Several advantages result from using hexagonal electrodes (pixel) as outlined above.

It has been found, both theoretically and practically, that corners on contact electrodes of the type used in measurements of the invention, constitute waste as the field which emanates from them disperses more rapidly, the sharper such corners are.

From a theoretical point of view circular electrodes would be the best as they have a minimum border length per unit area. In this present case they cannot be used as a dense cover of the entire surface is required. The electrode system of the invention is the optimum one, if only one shape of electrode elements is required. This comprises a plurality of hexagonal electrode elements in a geometrical arrangement where the hexagonal elements are provided in a close fit pattern, with a minimum distance between adjacent elements.

It is clear that the ratio of area to circumference is a better one with hexagons than with squares. A hexagonal electrode with sides of 1 cm length have a circumference of 6 cm and an area of 2.58 cm² versus a square of similar area (2.56 cm²) which has sides of 1.6 and a circumference of 6.4 cm.

According to a preferred embodiment of the invention, the array of electrodes of hexagonal shape are part of a generally planar printed circuit, which circuit also provides the required electrical connection for connecting at will at the same time any number and pattern of electrode sensors, and for the rapid switching between various numbers and configurations of the sensors used for specific measurements, the evaluation being effected generally by suitable computer devices.

A variety of hexagonal electrodes was evaluated, and it was found that hexagons with sides of about 10 mm give satisfactory results. This specific parameter is only indicative and not to be construed in a restrictive sense.

The electrode pattern of the invention is a highly effective one and generally good results are obtained up to a depth which equals about 3 times the linear dimensions of the electrode.

We claim:

1. A tumor detection system for detecting tumors in living human tissues based essentially on a determination of electric impedance values of localized regions of the tissues, comprising a probe comprising a plurality of planar hexagonal electrodes in a closely spaced geometric pattern, having a distance between adjacent electrodes, each of the electrodes being connected to detection circuitry;
   wherein the detection circuitry comprises:
   means for applying an AC signal to the tissue beneath each said electrode,
   means for sensing the electrical properties of the tissues based upon the AC signal applied to the tissue,
   means for providing an output indicative of the dielectric properties of each region of the tissue based upon signals indicating electrical properties of the tissues received from said means for sensing; and
   means for visually displaying the output indicative of dielectric properties;
   whereby tumors are detected by irregularities visible in said display means.

2. A system as claimed in claim 1, further comprising a printed circuit board wherein the hexagonal electrodes are part of a pattern on said printed circuit board.

3. A system according to claim 1, further comprising means for the repetitive application of said AC signal and means for evaluating the resulting signals.

4. A system as claimed in claim 1 in which said hexagonal electrodes are arranged in consecutive rows, and the rows of electrodes are displaced respective to a preceding row by half the width of the hexagonal electrode.

5. A system according to claim 1, where means are provided for switching from one electrode to a combination of a predetermined number of electrodes, and means for evaluating the results of such combination of electrodes.

6. A system according to claim 5, where measurements are made by combinations of electrodes at any given time.

7. A tumor detection system comprising:
   a multielement probe comprising a plurality of planar hexagonal electrodes in a closely spaced geometric pattern, having a distance between adjacent electrodes, each of the electrodes being connected to detection circuitry;
   wherein said detection circuitry comprises:
   means for determining the variation of the dielectric constant of localized regions of living human breast tissue as a function of frequency of a signal applied thereto and including automatic balancing bridge means which does not require nulling for each measurement;
   means for indicating differences in said variation over a plurality of said localized regions, said differences indicating the possible presence of a tumor;
   means for providing a swept frequency signal; and
   switching means for selectively and sequentially connecting invidual elements of said multielement probe to said balancing bridge and for connecting said probe elements not currently connected to said balancing bridge to said means for providing a swept frequency signal.

* * * * *